United States Patent [19]

Prachar et al.

[11] Patent Number: 5,426,415
[45] Date of Patent: Jun. 20, 1995

[54] BREATH ANALYZER FOR USE IN AUTOMOBILE IGNITION LOCKING SYSTEMS

[75] Inventors: Timothy J. Prachar, Des Moines; Douglas E. DeVries, Johnston; Michael W. Walter, Clive; Howard V. Block, Johnston, all of Iowa

[73] Assignee: Consumer Safety Technology, Des Moines, Iowa

[21] Appl. No.: 80,001

[22] Filed: Jun. 21, 1993

[51] Int. Cl.⁶ ............................................. G08B 23/00
[52] U.S. Cl. .................... 340/576; 340/632; 128/719
[58] Field of Search ............ 340/576, 279, 52 R, 340/53, 561, 632; 307/326; 180/272; 422/84; 128/718, 719

[56] References Cited

U.S. PATENT DOCUMENTS

| | | | |
|---|---|---|---|
| 4,039,852 | 8/1977 | Miyamoto et al. | 307/326 |
| 4,456,014 | 6/1984 | Buck et al. | 128/719 |
| 4,592,433 | 6/1986 | Simon | 180/272 |
| 4,678,057 | 7/1987 | Elfman et al. | 180/272 |
| 4,697,666 | 10/1987 | Collier et al. | 180/272 |
| 4,707,336 | 11/1987 | Jones | 128/719 |
| 4,738,333 | 4/1988 | Collier et al. | 180/272 |
| 4,749,553 | 6/1988 | Lopez et al. | 422/84 |
| 4,809,810 | 3/1989 | Elfman et al. | 180/272 |
| 4,901,058 | 2/1990 | Comeau et al. | 340/576 |
| 4,905,498 | 3/1990 | O'Donnell et al. | 340/576 |
| 4,912,458 | 3/1990 | Comeau et al. | 340/576 |
| 4,914,038 | 4/1990 | Jewitt | 340/576 |
| 4,926,164 | 5/1990 | Porter et al. | 340/576 |
| 5,020,628 | 6/1991 | Bigliardi et al. | 340/576 |
| 5,293,875 | 3/1994 | Stone | 128/719 |

Primary Examiner—John K. Peng
Assistant Examiner—Benjamin C. Lee
Attorney, Agent, or Firm—Henderson & Sturm

[57] ABSTRACT

An improved breath analyzing apparatus for use in an automobile ignition locking system. A breath sample tube receives a breath sample from a user. The breath sample tube is divided into a high pressure section and a low pressure section by an air flow restrictor. A pressure sensor is connected to the high pressure section to determine when a user is blowing into the breath analyzing apparatus. A temperature sensor measures the temperature of the breath sample to insure that it is the same temperature as human breath. A micropump propels a specified volume of the breath sample into a fuel cell which is used to determine the alcohol content. Control means converts the output of the fuel cell into a reading which represents the breath alcohol content of the breath sample. Heating elements warm the fuel cell when the ambient temperature drops below a specified level. The output of the fuel cell is adjusted based on the time it takes the fuel cell to reach its maximum output. A housing holds all the major components of the breath analyzing apparatus and contains a tamper switch therein which detects when the case is opened. A display on the housing shows the alcohol content of the breath sample as well as displaying instructions and messages for the user. The breath analyzer apparatus is used as part of an overall automobile ignition locking system which prohibits starting the car when the operator is intoxicating. The system also requires rolling retests to insure that the driver is still sober.

21 Claims, 3 Drawing Sheets

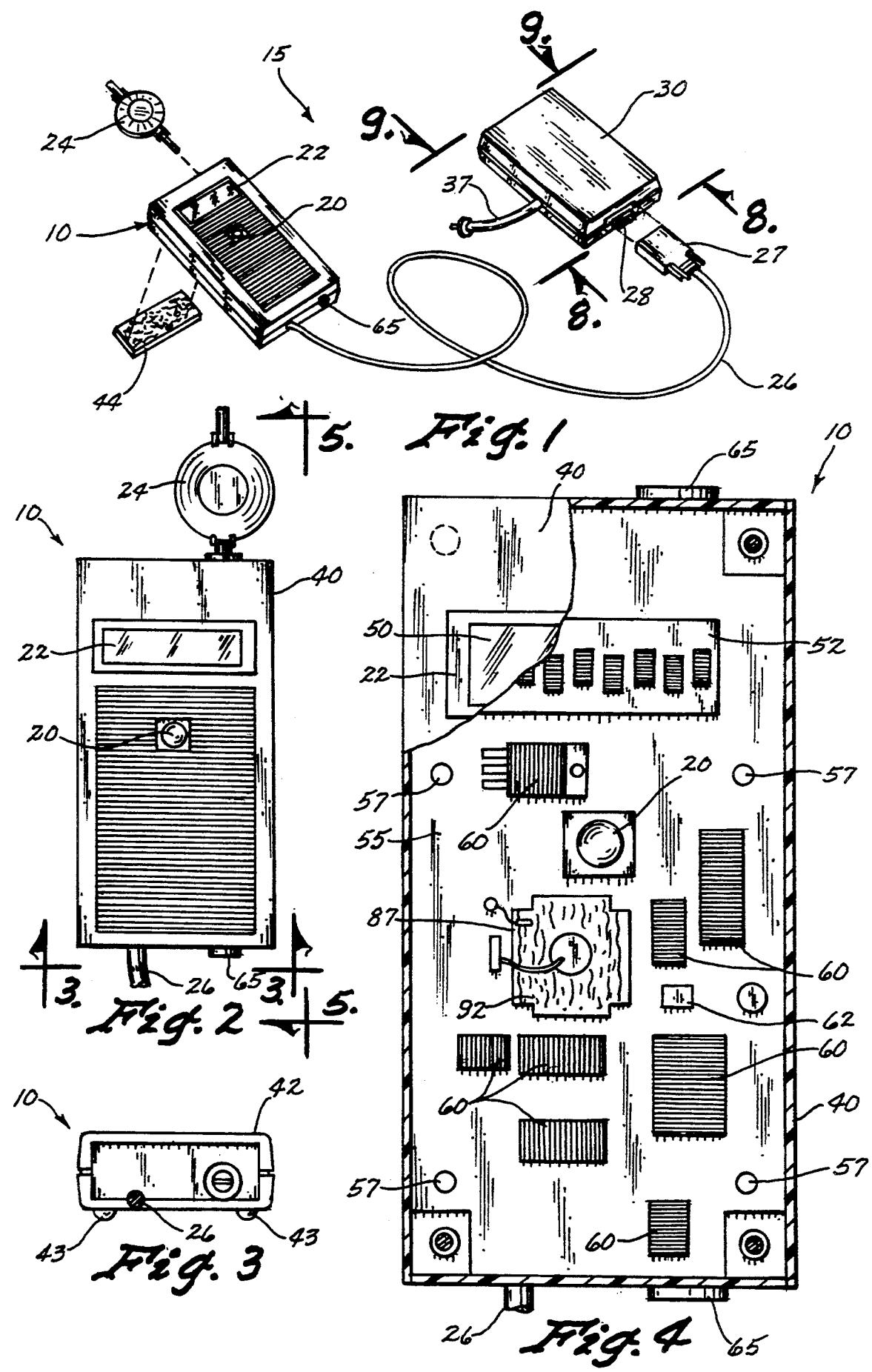

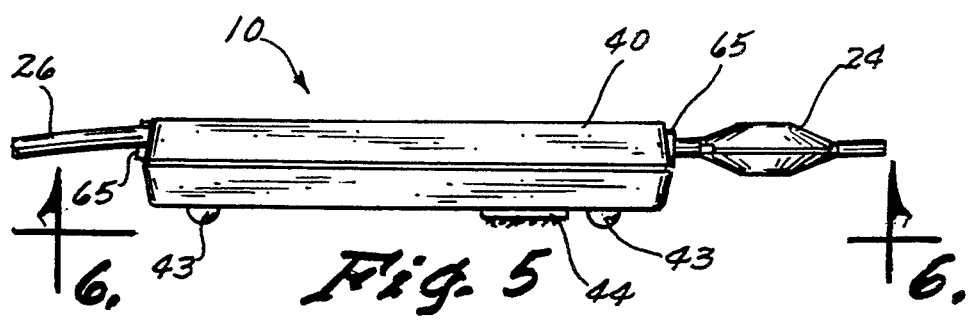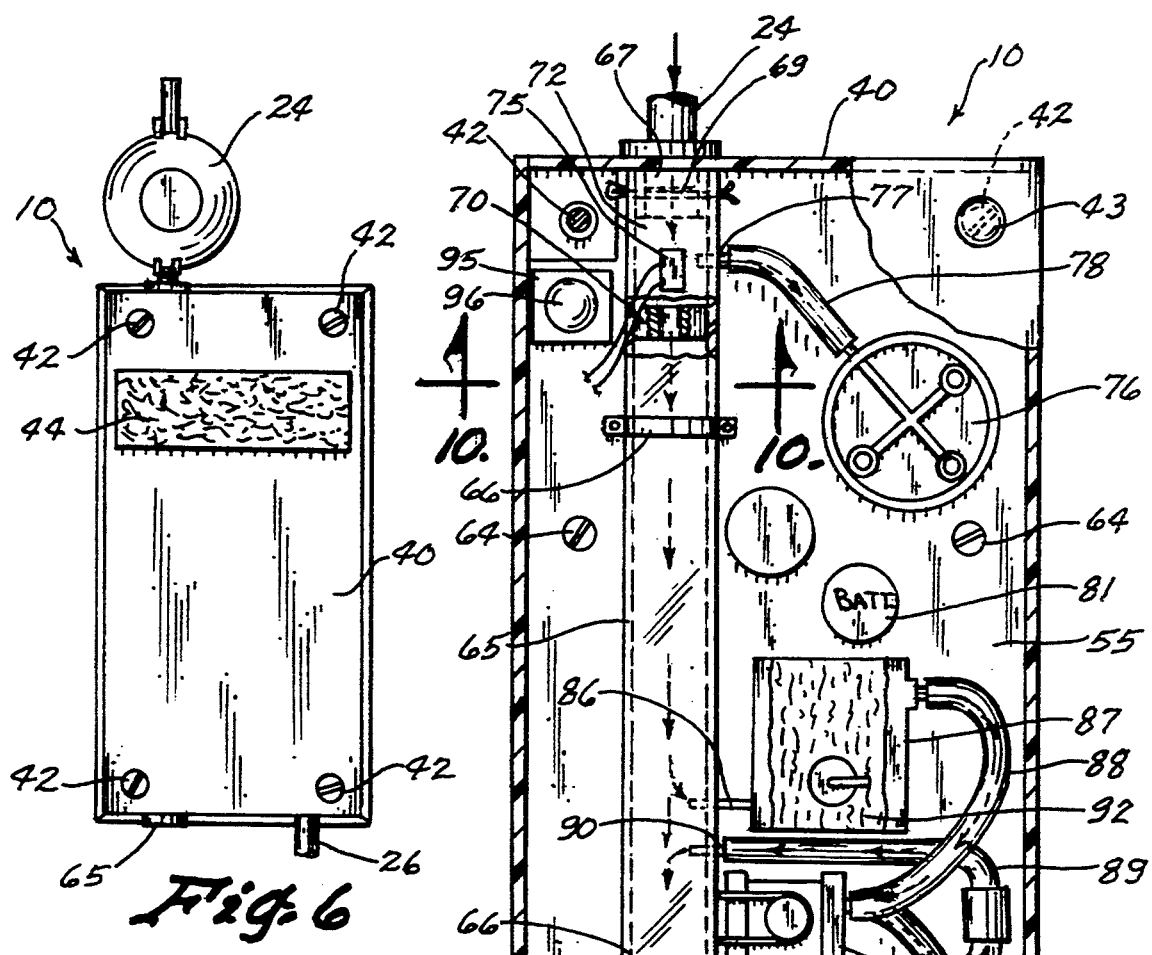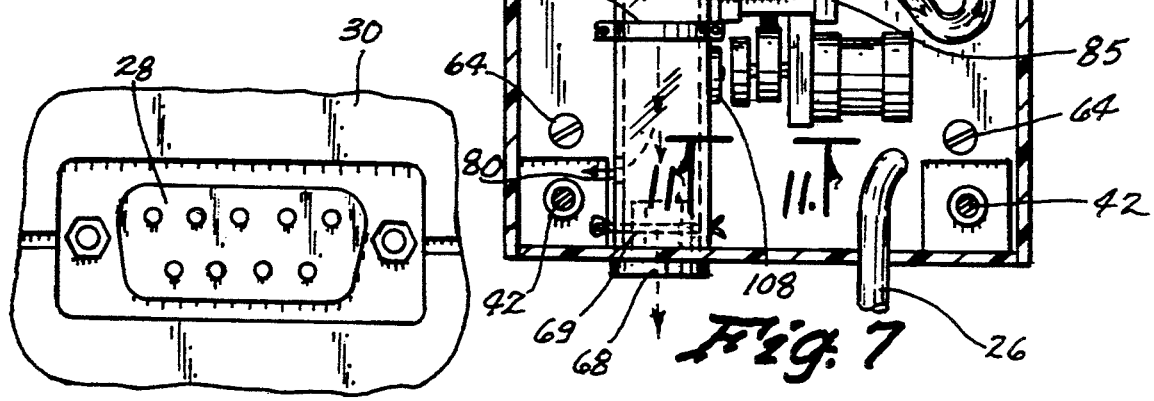

BREATH ANALYZER FOR USE IN AUTOMOBILE IGNITION LOCKING SYSTEMS

TECHNICAL FIELD

The present invention relates generally to breath analyzing devices and more specifically to an improved breath analyzing device used in an automobile ignition locking system which prevents a car from starting when the driver is intoxicated and which requires periodic rolling retests while the car is being operated.

BACKGROUND ART

Breath analyzing devices are used to determine the blood alcohol content of those who blow into the devices. These devices have become increasing popular with the increased effort by law enforcement to reduce drunk driving. While the traditional use of the breath analyzing devices has been by law enforcement officers to test a suspected intoxicated driver, the breath analyzing devices now are being used in combination with an ignition locking system to prevent an intoxicated driver from being able to start the vehicle.

The devices typically require the driver to blow into the breath analyzing device prior to starting the car. If the driver's breath alcohol level is below a predetermined level, the car will start. However, if the driver's breath alcohol level is too high, the car will not start. Drivers typically use breath analyzing devices in combination with ignition locking systems in one of two situations. The first situation is when ordered to do so by a court. Courts are finding these systems to be effective in controlling drivers with multiple incidents of driving while intoxicated. The second situation is voluntary use by drivers concerned about driving or getting apprehended while driving under the influence of alcohol. Additional uses such as in commercial fleets, taxis, buses and the like also offer a suitable environment for these types of systems.

The most commonly used alcohol sensor is the gas detection tube. However, a better alcohol sensor is the fuel cell. The fuel cell is a more accurate device for measuring the alcohol content in a breath sample. Thus there is a need for a breath analyzer which utilizes a fuel cell.

The alcohol sensing devices are typically very sensitive to temperature. Various attempts have been made to minimize the effect temperature change, especially as the alcohol sensor gets colder, has on the accuracy of the reading. A previously tried method allowed the sensor to get cold and then attempted to compensate the result utilizing an algorithm dependent upon temperature. Other approaches warm the breath analyzer to keep the alcohol sensor warm. This is costly in terms of energy consumption. Thus there is a need for a combination alcohol sensor and heating mechanism which effectively and efficiently maintains the alcohol sensor in a temperature range so as not to jeopardize reliability.

The output of alcohol sensors are prone to vary due to several factors. Time, temperature and other environmental conditions can all cause the output of the alcohol sensor to be inaccurate. Thus there is a need for a compensating algorithm which accurately compensates the output of an alcohol sensor.

In light of the foregoing, an improved breath analyzing device used in combination with an ignition locking system is needed which utilizes a highly accurate alcohol sensor, which delivers a precise amount of breath sample to the alcohol sensor, which does not require mathematical corrections to compensate for the drop in ambient temperature, and which requires the user to perform rolling retests while operating the vehicle.

DISCLOSURE OF THE INVENTION

The present invention relates generally to breath analyzing devices and more specifically to an improved breath analyzing device used in an automobile ignition lock system which prevents a car from starting when the driver is intoxicated and which requires periodic rolling retests while the car is being operated. A breath analyzing device comprises a housing for holding the individual components through which is disposed a breath sample tube. The breath sample tube is divided into a high pressure section and a low pressure section by an air flow restrictor. A pressure sensing device connected to the high pressure section detects when a user is blowing into the analyzer device. The pressure sensor must remain triggered for several seconds before the analyzer device will begin sampling the breath sample. This insures that only deep lung air will be sampled. A temperature sensor is also connected to the high pressure section of the breath sample tube such that the temperature of the sample can be compared to the known temperature of human breath to help eliminate the possibility of intentional misuse by the user.

In the low pressure section of the breath sample tube, a portion of the breath sample is propelled through an inlet tube, through a fuel cell, through an outlet tube and back into the breath sample tube by a micropump. The micropump is used to propel an accurate size sample into the fuel cell to insure an accurate blood alcohol reading.

Positioned near the fuel cell are heating elements. These heating elements warm the fuel cell when the ambient temperature drops below the ideal temperature range for the fuel cell. These heating elements respond proportionally to the drop in temperature. Thus the colder the temperature, the more heat they put out. This controlled heating of the fuel cell helps to guarantee a blood alcohol content reading which is accurate.

Control devices in the breath analyzer device takes a signal from the fuel cell and converts it into a breath alcohol reading. This reading is adjusted or compensated based on the time it takes the fuel cell to reach its peak output. This adjustment or compensation is used as an additional measure to make the end reading as accurate as possible. The final reading is presented to the user by means of a display which is connected to the housing. The display can also be used to present instructions and messages to the user.

The housing of the breath analyzing device includes a tamper switch to detect when a user tries to open the analyzer device. The tamper switch is a button which is secured to one half of the housing and is compressed by the other half of the housing. The unit cannot be opened without the tamper switch being decompressed and a tamper signal being triggered.

The breath analyzing device is combined with an ignition locking system which disables the starting mechanisms of the car unless a satisfactory sample is blown into the breath analyzer device. Part of this system includes means for storing all of the data associated with the number, the time and the results of the tests. The system also requires the driver of the vehicle to pass periodic rolling retests after the vehicle has been started. If the driver fails a retest, an appropriate warning response occurs such as flashing lights, activating the vehicle's horn or both.

An object of the present invention is to provide an improved breath analyzing device.

Another object of the present invention is to provide an improved breath analyzing device which is used in an automobile ignition lock system.

A further object of the present invention is to provide an improved breath analyzing device which is used in an automobile ignition locking system which requires rolling retests.

Another object of the present invention is to provide an improved breath analyzing device capable of detecting tamper attempts.

Still another object of the present invention is to provide an improved breath analyzing device which uses a fuel cell to determine the alcohol content in the breath sample.

Still another object of the present invention is to provide an improved breath analyzing device which activates a heating mechanism to heat the fuel cell when the ambient temperature drops below a specified level.

Still another object of the present invention is to provide an improved breath analyzing device which provides more reliable breath sample alcohol content readings by adjusting the reading based on the time it takes the fuel cell to reach its peak output.

Still another object of the present invention is to provide an improved breath analyzing device which utilizes a micropump for delivering a sample to the fuel cell.

Other objects, advantages, and novel features of the present invention will become apparent from the following detailed description of the invention when considered in conjunction with the accompanying drawings.

BRIEF DESCRIPTION OF THE DRAWINGS

FIG. 1 is an exploded perspective view of a breath analyzer used with an automobile ignition locking unit built in accordance with the present invention;

FIG. 2 is a front view of the breath analyzer of FIG. 1;

FIG. 3 is a bottom view taken along line 3—3 of the breath analyzer of FIG. 2;

FIG. 4 is a partial horizontal sectional view showing the front portion of the circuit board inside the breath analyzer of the present invention;

FIG. 5 is a side elevational view taken along line 5—5 of the breath analyzer of FIG. 2;

FIG. 6 is a back view taken along line 6—6 of the breath analyzer of FIG. 5;

FIG. 7 is a partial horizontal sectional view showing the back portion of the circuit board inside the breath analyzer of the present invention and showing most of the major components used for determining the alcohol content of a breath sample;

FIG. 8 is a bottom view taken along line 8—8 of the vehicle interface device of FIG. 1;

BEST MODES FOR CARRYING OUT THE INVENTION

Figure 9:
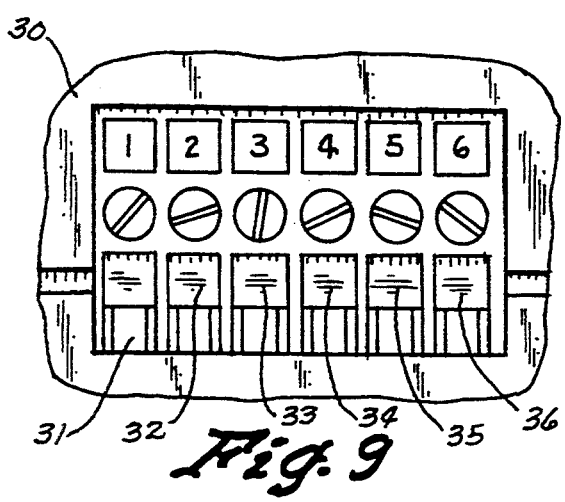
FIG. 9 is a top view taken along line 9—9 of the vehicle interface device of FIG. 1.

Referring now to the drawings wherein like reference numerals designate identical or corresponding parts throughout the several views, FIG. 1 shows a breath analyzer (10) for measuring the alcohol content of a breath sample used in an ignition locking system (15) built in accordance with the present invention. The ignition locking system (15) is designed to prevent an intoxicated driver from operating a motor vehicle. A driver of a vehicle within which the present invention has been installed must pass a breath test prior to starting the vehicle.

In a typical situation, a driver initiates a start up procedure by pressing a button (20) on the breath analyzer (10). The driver waits for the breath analyzer (10) to signal that it is ready to test the driver's breath. The breath analyzer (10) includes a display (22) which is used to show messages and instructions to the driver as well as displaying the results of the breath test. When the breath analyzer (10) indicates that it is ready to test, the driver blows into a mouthpiece (24) which is inserted into the breath analyzer (10). Various mouthpieces could be used in the present invention but the type which additionally operates as a saliva trap is the best. The driver must blow into the breath analyzer (10) for at least five seconds before a sample will be taken. This insures that only deep lung air will be tested.

After approximately five (5) seconds, the breath analyzer (10) samples the driver's breath and determines its alcohol content. If the alcohol content is below a predetermined limit, the driver passes the test and breath analyzer signals to the vehicle interface device (30) that the car may be started. The vehicle interface device (30) is connected to the vehicle's starter and keeps the starter disabled until a breath test is passed. If the test is failed, a fail signal will be transmitted to the vehicle interface device (30) and the vehicle's starter will be remain disabled.

The breath analyzer (10) is connected to the ignition locking system (15) vehicle interface device (30) by a cable (26). The cable (26) connects to the vehicle interface device (30) using a standard 9-pin, D-shaped, male-female connection. The male connector (27) is attached to the cable (26) and the female connector (28) is disposed on the vehicle interface device (30). Referring to FIG. 8, the female connector (28) disposed on the vehicle interface box (30) is shown. The cable (26) allows for communication of information between the breath analyzer (10) and the vehicle interface device (30). Additionally, the cable (26) is used to supply power to the breath analyzer (10). The power can either come from a battery source located in the vehicle interface device (30) or from the vehicle's electrical system. The power from the vehicle's electrical system is channelled through the vehicle interface device (30).

Referring to FIG. 9, wire connectors (31-36) are shown disposed on the vehicle interface device. These wire connectors (31-36) are used to connect the vehicle interface device (30) to the vehicle's battery, starter, lights and horn. Referring again to FIG. 1, a vacuum interface tube (37) allows the vehicle interface device to know if the vehicle's engine is operating.

After the vehicle is started, the breath analyzer (10) will require periodic retesting of the driver's breath. These periodic retestings are called rolling retests because the driver need not stop the vehicle. The breath analyzer (10) will indicate on the display (22) that the driver must blow into the breath analyzer (10) again. An audio alarm (23), as seen in FIG. 7, such as a small beeper, buzzer or horn, is disposed in the breath analyzer (10) and provides an additional, audio signal to indicate to the driver the need to take another breath test.

If the driver does not pass a breath test within a relatively short time after the unit signals for a rolling retest, either by having a breath sample which exceeds the limit or by failing to even take the test, the breath analyzer (10) signals the vehicle interface device (30) that the driver has failed to pass the breath test. This message will also be shown on the display (22) and the display will instruct the driver to immediately pull the car over and shut off the vehicle. Since the vehicle is moving and disabling the starter will not affect the operation of the vehicle, the vehicle interface device (30) activates a warning system. This warning system typically includes flashing the vehicle's external lights, periodically activating the vehicle's horn, or both. This activation of the warning system will continue until a breath test is passed or the vehicle is shut off.

The breath analyzer (10) includes a microprocessor to control all of the above described operations, memory capacity and a real time clock. The real time clock maintains the current time and date. The processor is a Dallas DS5000FP microcontroller and includes internal timer mechanisms. The memory is composed of two 32K×8 SRAMS. These chips were selected for their low current requirements. One of the memory chips is used to store the software required by the microcontroller to control the breath analyzer (10). The other memory chip is used to record a log of all of the events occurring with the breath analyzer (10). The event log includes the date, time and results of each test. Additionally, tamper protection devices are included in the breath analyzer (10). The event log records information relating to these various tamper protection devices. Typically, this information is periodically downloaded and reviewed by whatever party is requiring the driver to have the device in the vehicle.

Referring to FIGS. 2, 3, 5 and 6, the breath analyzer (10) has a plastic housing (40) to hold the major components of the device. The housing (40) is made up of a bottom and a top portion and is held together by a plurality of fasteners (42). Rubber feet (43) are placed over the fasteners (42). The rubber feet (43) serve to provide a cushioned, non-slip base for the breath analyzer (10) as well as remove from sight the fasteners (42) which allow access to the major components. A hook and loop fastener (44) can also be attached to the breath analyzer (10) and used to hold the breath analyzer (10) stationary in the vehicle between tests. The mouthpiece (24) is shown inserted into the breath analyzer (10).

Referring to FIG. 4, the breath analyzer (10) is shown with the top portion of the housing (40) cut away. The display (22) includes a window (50) disposed in the top portion of the housing (40) and an internal LED, 1 line by 8 character display (52). Displays of this type are commonly known in the industry and this particular display is manufactured by Hewlett-Packard. The display (52) is mounted on a circuit board (55). The circuit board (55) is used to hold the major components of the breath analyzer (10) and provides a means for electrical communication between the computer and electrical components. The circuit board (55) has four holes (57) which are used to fasten the circuit board (55) to the top portion of the housing (40).

Various computer and electrical components (60) are shown electrically attached to the circuit board (55). The components (60) include the microcontroller, the memory chips, the real time clock, the interface chip, for the display (52) and other power control devices. An ambient temperature sensor (62) is shown connected to the circuit board (55). The function of the ambient temperature sensor will be discussed below.

Referring to FIG. 7, the breath analyzer (10) is shown with the bottom portion of the housing (40) cut away and showing the opposite side of the circuit board (55) shown in FIG. 4. The circuit board (55) is shown attached to the top portion of the housing (40) with four fasteners (64). A breath sample tube (65) is disposed through the housing (40) of the breath analyzer (10). The breath sample tube (65) is connected to the circuit board using two plastic straps (66). The breath sample tube (65) has a first opening (67) through which a breath sample enters. The mouthpiece (24) is shown inserted into the first opening (67). The breath sample tube (65) also has a second opening (68) though which the breath sample exits.

Tamper pins (69) are positioned in close proximity to the first opening (67) and the second opening (68) and bisect the two openings. The tamper pins (69) placed in close proximity to the two openings help to impede either the accidental or intentional insertion of foreign materials or objects into the breath sample tube (65).

An air flow restrictor (70) is positioned inside the breath sample tube (65). The air flow restrictor (70) is a disk shaped piece of plastic with a center hole which is relatively small with respect to the inside diameter of the breath sample tube (65). The air flow restrictor (70) restrains the flow of the breath sample blown into the breath sample tube (65) and divides the breath sample tube (65) into two sections. The first section is a high pressure section (72) which is comprised of the section of the breath sample tube (65) between the first opening (67) and the air flow restrictor (70). The second section is a low pressure section (73) which is comprised of the section of the breath sample tube (65) between the air flow restrictor (70) and the second opening (68).

A breath sample temperature sensor (75) is attached to the breath sample tube (65) in the high pressure section (72). The breath sample temperature sensor (75) measures the temperature of the breath sample. The temperature sensed is communicated to the microcontroller which it compares to the known temperature of human breath. If the sensed temperature varies too greatly from the known value, the breath analyzer (10) will not test the breath sample. This feature is used to help deter a driver from blowing some other source of forced air into the breath analyzer (10). A similar humidity device can also be attached but is not shown in this embodiment of the invention.

A pressure sensor (76) is connected to the high pressure section (72) of the breath sample tube (65) by means of a small tube (77) inserted into the breath sample tube and a small rubber hose (78). The pressure sensor (76) is a diaphragm type pressure switch and senses the air pressure generated by a user or driver blowing into the breath sample tube (65). The pressure sensor (76) is electrically connected to the microcontroller and sends a signal to the microcontroller that a breath sample is being sensed. The microcontroller makes sure that the pressure sensor (76) senses a sample for several seconds before continuing with the test.

After flowing through the air flow restrictor (70), the breath sample flows through the low pressure section of the breath sample tube (65) and out the second opening (68). A secondary breath sample exit hole (80) is provided to insure that the breath sample freely flows through the breath sample tube (65). The secondary breath sample exit hole (80) is positioned inside the housing (40) and prevents the breath analyzer (10) from being fooled by a user who covers the second opening (68) while blowing into the device.

A battery (81) is connected to the circuit board (55) and provides power to the microcontroller, memory chips and real time clock in the event that power is not supplied by the vehicle interface device (30).

The actual sample for the testing of the breath sample is taken from the low pressure section (73) of the breath sample tube (65). The breath sample is propelled out of the sample tube (65), through a testing loop, and back into the sample tube (65) by a micro pump (85). The micropump propels the sample from the breath sample tube (65), through an inlet tube (86), into a fuel cell (87), through a first tube (88), through the micro pump (85), through a second tube (89), through the outlet tube (90), and back into the breath sample tube (65). In the best embodiment of the present invention, the inlet tube (86) is placed before the outlet tube (90) with respect to the flow of the breath sample. Additionally, both tubes are placed a sufficient distance from the air flow restrictor (70) to minimize the venturi effect. Utilizing an inlet tube (86) and an outlet tube (90) which are of the same diameters and which are similarly inserted into the breath tube creates a situation where neither tube has a greater pressure placed on it and thus there will not be any undesired air flow through the testing loop.

The actual testing of the breath sample occurs in the fuel cell (87). The fuel cell (87) is an electrochemical device that generates current flow between its electrodes when a breath sample containing alcohol vapor is introduced into it. The fuel cell (87) consists of an anode and a cathode separated by an acidic electrolyte. The working electrode is the anode and physically it forms one of the walls of the cell chamber. Thus, when a sample is introduced into the cell's chamber, the sample comes into contact with the anode. The cathode is exposed to the outside atmosphere where it reacts with the oxygen present in the atmosphere. At the anode, alcohol molecules in the breath sample are oxidized, while atmospheric oxygen molecules at the cathode are simultaneously reduced. In order for the reaction to take place, electrons must be exchanged between the anode and the cathode. This electron exchange, or current flow, is in proportion to the number of alcohol molecules present in the breath sample.

Several factors can effect the fuel cell's output, including the concentration of oxygen at the cell's cathode, the temperature of the cell, and the age and fatigue level of the cell. Since the fuel cell's output is proportional to the number of alcohol molecules available in the sample for oxidation, and since what is being determined is breath alcohol concentration, or alcohol per unit volume, it is crucial that the volume of the sample taken into the cell be known and consistent for accuracy and repeatability of the measurement. The desired sample size for the present invention is 0.5 ml.

The fuel cell (87) has operating limitations placed on it by the manufacturer based on temperature. In order to keep the fuel cell's temperature within usable limits, a continuously variable self-regulating heating element (92) is positioned around the fuel cell (87) and is energized when the ambient temperature falls below a fixed value. The ambient temperature is measured by the ambient temperature sensor (62), shown in FIG. 4. As the ambient temperature falls, power delivered to the heating element (92) is gradually increased. Conversely, when the ambient temperature rises, power delivered to the heating element (92) is gradually decreased. When the ambient temperature rises above a predetermined, fixed level, the heating element (92) is disabled.

To compensate for factors which effect the rate at which the alcohol present in the breath sample is oxidized (and therefore the fuel cell's output for that sample), a unique and accurate method for oxidation rate compensation is implemented. For each sample taken, the time required for the output of the fuel cell (87) to rise to its maximum level is measured and recorded. This "time to peak" correlates strongly with the rate of oxidation of the alcohol in the sample and is therefore effective in compensating for any change in the output of the cell due to variances in oxidation rates.

The fuel cell (87) generates a current proportional to the amount of alcohol detected in the sample. This current is routed through a 390 ohm resistor (not shown) to generate a voltage. The peak voltage across this resistor is typically less than 12 mV. This voltage is fed into a precision amplifier configured for a gain of 303, and is selected for a very low offset voltage (30 $\mu V$) and low gain-bandwidth product (0.5 MHz). The output of this amplifier is then directed to an analog-to-digital converter, where positive voltages are measured from 0 to 5 volts in steps of 16.1 $\mu V$ and negative voltages from $-5$ to 0 in 32.2 $\mu V$ steps.

Figure 10:
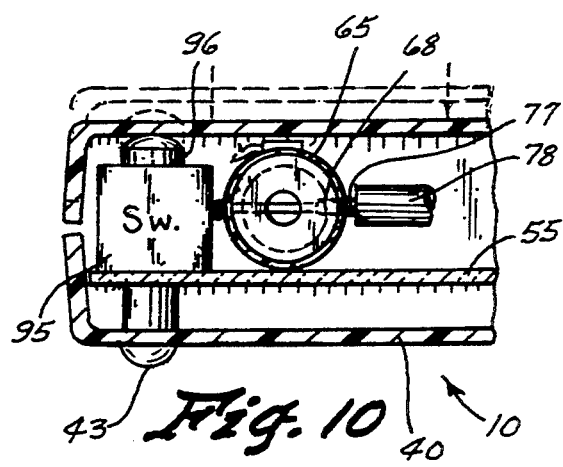
FIG. 10 is a partial vertical sectional view taken along line 10—10 of FIG. 7, showing the housing tamper switch.

Referring now to FIG. 10, a tamper switch (95) is provided to allow for detection of an unauthorized opening of the housing (40) of the breath analyzer (10). The tamper switch (95) is mounted on the circuit board (55) which in turn is secured to the top portion of housing (40). The tamper switch (95) is electrically connected to the microcontroller. When the bottom portion of the housing (40) is secured to the top portion of the housing (40), a button (96) on the tamper switch (95) is depressed. When the housing (40) is opened, that is, when the top and bottom portions are not secured together, as shown in dashed lines, the button (96) on the tamper switch (95) is not depressed and the tamper switch (95) triggers and a tamper condition signal is sent to the microcontroller. The microcontroller can either set off an alarm, record the tamper attempt in the event log, or both.

Figure 11:
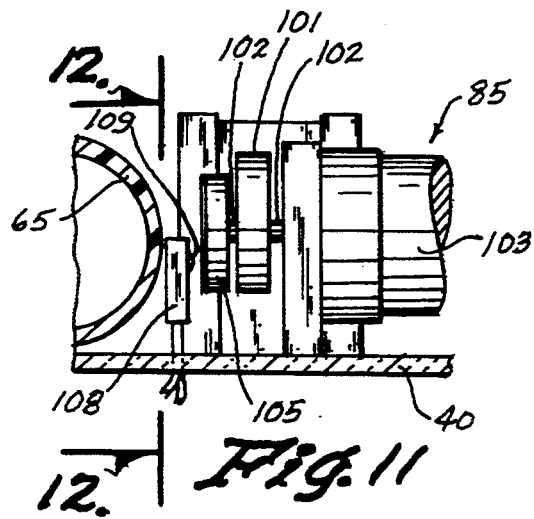
FIG. 11 is a partial vertical sectional view taken along line 11—11 of FIG. 7, showing the micropump used to propel a specific amount of breath sample into the fuel cell.
Figure 12:
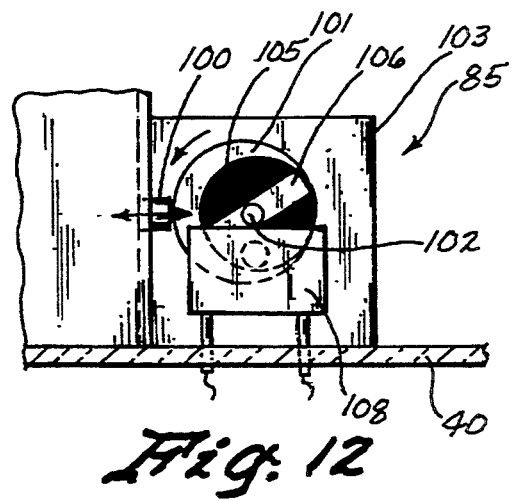
FIG. 12 is a side view taken along line 12—12 of the micropump of FIG. 11.

Referring to FIGS. 11 and 12, the micropump (85) used to propel the breath sample through the testing loop is shown. The micropump (85) includes a diaphragm type pump (110). The diaphragm (not shown) of the pump (110) is reciprocated by a piston (100). The piston (100) is connected to and reciprocated by a crank (101). The crank (101) is turned by a crankshaft (102) which is turned by a small, electrical, DC motor (103).

In order to insure that the precise amount of breath sample is propelled into the fuel cell (87), the number of crank revolutions made by the motor (103) is counted. The number of pump cycles will be the same as the number of crank revolutions. The counting of the crank revolutions is accomplished by placing a black disk (105) on the crankshaft (102) such that it turns at the same speed as the crank (101). A white diameter line (106) is painted on the black disk (105). The white line (106) operates as a detectable division on the black disk (105). A sensor (108) is positioned in front of the black disk (105). As the black disk (105) turns, a sensor eye (109) on the sensor (108) detects the white line (106) as it passes by the sensor eye (109). Thus, every other detection of the white line (106) by the sensor eye (109) corresponds to one complete pump cycle since there are two detections per revolution.

In the present invention, 70 detections, or 35 pump cycles, propels the precise desired amount of breath sample into the fuel cell (87). The sensor (108) is electrically connected to the microcontroller which activates and deactivates the motor (103) of the micropump (85). However, the microcontroller does not wait until the 70th detection to deactivate the motor (103) because after deactivation the motor (103) of the micropump (85) will continue to coast for several more revolutions. Therefore, the motor (103) must be deactivated sometime before the 70th detection in order to get a total of 35 pump cycles. The number of half revolutions, or individual detections, the motor will coast is a function of the motor and the temperature. The microcontroller determines how early to deactivate the motor (103) based on the information it has stored in a table whose entries vary with respect to temperature.

Additionally, the microcontroller is able to learn from each test. Thus, during a particular test, the microcontroller ascertains the ambient temperature using the ambient temperature sensor (62) and will recall how much coast there was for this motor the last time a test was taken at this temperature. It will use this number to determine when to deactivate the motor (103). If the total sensor detections comes up 70 for the current test, then nothing changes in the microcontroller's table. However, if the number is not 70, the table will be changed and the new coasting factor will inserted for the old factor for this testing temperature.

Obviously, many modifications and variations of the present invention are possible in light of the above teachings. It is therefore to be understood that, within the scope of the appended claims, the invention may be practiced otherwise than as specifically described.

We claim:

1. A breath analyzer for measuring the alcohol content of a breath sample for use in an ignition locking system for preventing operation of a vehicle when the driver is intoxicated, comprising:

a housing;

a breath sample tube disposed through said housing for communicating a breath sample through said housing, said breath sample tube having a first opening wherein a breath sample enters and a second opening wherein a breath sample exits;

an inlet tube inserted into said breath sample tube;

an outlet tube inserted into said breath sample tube;

a fuel cell operatively connected to said inlet tube and said outlet tube, said fuel cell having an output which depends upon the alcohol content of the breath sample and the volume of the breath sample;

means positioned in close proximity to said fuel cell for heating said fuel cell;

means for propelling a specific volume of breath sample from said breath sample tube, through said inlet tube, through said fuel cell, through said outlet tube, and back into said breath sample tube;

a display operatively attached to said housing;

means for controlling said breath analyzer, said controlling means including means for controlling said heating means, means for activating and deactivating said propelling means, means for measuring and converting said output of said fuel cell into a breath alcohol content reading, and means for transmitting said breath alcohol content reading to said display means;

an ambient temperature sensor disposed in said housing and operatively connected to said controlling means;

an ignition locking system operatively and electrically connected to said breath analyzer and operatively and electrically connected to said vehicle wherein said ignition locking system prevents said vehicle from starting if it receives a signal from said controlling means that the breath alcohol content reading is above a predetermined limit;

an air flow restrictor disposed within said breath sample tube, said air flow restrictor dividing said breath sample tube into a high pressure section and a low pressure section;

a pressure sensor operatively connected to said breath sample tube in said high pressure section wherein said pressure sensor is triggered when a driver blows into said breath analyzer;

means for communicating to said controlling means that said pressure sensor is triggered; and wherein said inlet tube and said outlet tube are inserted into said breath sample tube in said low pressure section.

2. The breath analyzer of claim 1:

including a breath sample temperature sensor positioned on said high pressure section of said breath sample tube, said breath sample temperature sensor having an output corresponding to the temperature of the breath sample and being operatively connected to said controlling means; and wherein said controlling means includes means for comparing said output of said sample temperature sensor to a predetermine temperature wherein said breath analyzer will not analyze said breath sample if the temperature of said breath sample varies too greatly from the predetermined temperature.

3. The breath analyzer of claim 2 wherein said controlling means of said breath analyzer includes means for requiring periodic retesting of the drivers breath after the vehicle has been started.

4. The breath analyzer of claim 3 wherein said controlling means includes means for signalling to the driver that a retest was failed and that the vehicle must be turned off.

5. The breath analyzer of claim 4 wherein said ignition locking system includes means for generating a warning signal that a retest has been failed and the vehicle has not been stopped.

6. The breath analyzer of claim 5 wherein means for generating a warning signal comprises at least one of flashing the external lights of said vehicle and periodically activating the horn of said vehicle.

7. The breath analyzer of claim 2 wherein said propelling means comprises a micro pump, said micro pump comprising a diaphragm-type pump, a piston for reciprocating the diaphragm of said diaphragm-type pump, a crank and crankshaft operatively connected to said piston for reciprocating said piston, and an electric motor for revolving said crank and said crank shaft.

8. The breath analyzer of claim 7 including means for counting the revolutions of said crank and means for deactivating said motor when a predetermined number of revolutions have occurred wherein said specific volume of breath is controlled by counting the revolutions of said crank and deactivating said motor at the appropriate time.

9. The breath analyzer of claim 8 wherein said motor is selectively deactivated a predetermined number of revolutions short of the overall desired number of revolutions to compensate for the coasting characteristics of the motor.

10. The breath analyzer of claim 9 wherein said predetermined number of revolutions is a function of the ambient temperature sensed by said ambient temperature sensor.

11. The breath analyzer of claim 8 wherein counting means includes a detectable division attached to said crank and a sensing device for detecting said detectable division.

12. The breath analyzer of claim 2 including:
means associated with said housing for opening said housing whereby components disposed in said housing of said breath analyzer are made accessible; and
a tamper switch disposed within said housing and operatively connected to said controlling means, said tamper switch positioned such that it will be triggered when said housing is opened.

13. The breath analyzer of claim 12 including a secondary breath sample exit hole disposed in said breath sample tube and positioned within said housing and in close proximity to said second opening wherein a breath sample exits.

14. The breath analyzer of claim 13 including tamper pins position in close proximity to said first opening wherein a breath sample enters and said second opening wherein a breath sample exits, wherein said tamper pins impede the insertion of foreign materials and objects into said breath sample tube.

15. The breath analyzer of claim 2 including a mouthpiece inserted into said first opening wherein a breath sample enters.

16. The breath analyzer of claim 2 wherein said breath analyzer utilizes power provided by said ignition locking system and including a battery for providing power to said controlling means when said ignition locking system cannot provide sufficient power.

17. The breath analyzer of claim 2 including means associated with said controlling means for adjusting the breath alcohol content reading based on the time it takes the fuel cell to reach its maximum output.

18. The breath analyzer of claim 2 wherein said means for controlling said heating means includes means for varying the heat generated by said heating means dependent upon the ambient temperature sensed by said ambient temperature sensor.

19. The breath analyzer of claim 1 including means for delaying the activation of said propelling means for a predetermined period of time after said pressure sensor is triggered whereby the time delay insures that only a deep lung sample will be tested.

20. The breath analyzer of claim 19 wherein said predetermined period of time is five (5) seconds.

21. A breath analyzer for measuring the alcohol content of a breath sample for use in an ignition locking system for preventing operation of a vehicle when the driver is intoxicated, comprising:

a housing;
a breath sample tube disposed through said housing for communicating a breath sample through said housing, said breath sample tube having a first opening wherein a breath sample enters and a second opening wherein a breath sample exits;
an inlet tube inserted into said breath sample tube;
an outlet tube inserted into said breath sample tube;
a fuel cell operatively connected to said inlet tube and said outlet tube, said fuel cell having an output which depends upon the alcohol content of the breath sample and the volume of the breath sample;
means positioned in close proximity to said fuel cell for heating said fuel cell;
means for propelling a specific volume of breath sample from said breath sample tube, through said inlet tube, through said fuel cell, through said outlet tube, and back into said breath sample tube;
a display operatively attached to said housing;
means for controlling said breath analyzer, said controlling means including means for controlling said heating means, means for activating and deactivating said propelling means, means for measuring and converting said output of said fuel cell into a breath alcohol content reading, and means for transmitting said breath alcohol content reading to said display means;
an ambient temperature sensor disposed in said housing and operatively connected to said controlling means;
an ignition locking system operatively and electrically connected to said breath analyzer and operatively and electrically connected to said vehicle wherein said ignition locking system prevents said vehicle from starting if it receives a signal from said controlling means that the breath alcohol content reading is above a predetermined limit;
an air flow restrictor disposed within said breath sample tube, said air flow restrictor dividing said breath sample tube into a high pressure section and a low pressure section;
a pressure sensor operatively connected to said breath sample tube in said high pressure section wherein said pressure sensor is triggered when a driver blows into said breath analyzer;
means for communicating to said controlling means that said pressure sensor is triggered;
wherein said inlet tube and said outlet tube are inserted into said breath sample tube in said low pressure section;
means for delaying the activation of said propelling means for a predetermined period of time after said pressure sensor is triggered whereby the time delay insures that only a deep lung sample will be tested;
a breath sample temperature sensor positioned on said high pressure section of said breath sample tube, said breath sample temperature sensor having an output corresponding to the temperature of the breath sample and being operatively connected to said controlling means;
wherein said controlling means includes means for comparing said output of said sample temperature sensor to a predetermine temperature wherein said breath analyzer will not analyze said breath sample if the temperature of said breath sample varies too greatly from the predetermined temperature;
means associated with said housing for opening said housing whereby components disposed in said housing of said breath analyzer are made accessible;

a tamper switch disposed within said housing and operatively connected to said controlling means, said tamper switch positioned such that it will be triggered when said housing is opened;

a secondary breath sample exit hole disposed in said breath sample tube and positioned within said housing and in close proximity to said second opening wherein a breath sample exits;

tamper pins position in close proximity to said first opening wherein a breath sample enters and said second opening wherein a breath sample exits, wherein said tamper pins impede the insertion of foreign material and objects into said breath sample tube;

wherein said breath analyzer utilizes power provided by said ignition locking system;

a battery for providing power to said controlling means when said ignition locking system cannot provide sufficient power;

wherein said controlling means of said breath analyzer includes means for requiring periodic retesting of the drivers breath after the vehicle has been started;

wherein said controlling means includes means for signalling to the driver that a retest was failed and that the vehicle must be turned off;

wherein said ignition locking system includes means for generating a warning signal that a retest has been failed and the vehicle has not been stopped, said means for generating a warning signal comprises at least one of flashing the external lights of said vehicle and periodically activating the horn of said vehicle;

wherein said propelling means comprises a micro pump, said micro pump comprising a diaphragm-type pump, a piston for reciprocating the diaphragm of said diaphragm-type pump, a crank and crankshaft operatively connected to said piston for reciprocating said piston, and an electric motor for revolving said crank and said crank shaft;

means for counting the revolutions of said crank and means for deactivating said motor when a predetermined number of revolutions have occurred wherein said specific volume of breath is controlled by counting the revolutions of said crank and deactivating said motor at the appropriate time;

wherein said counting means includes a detectable division attached to said crank and a sensing device for detecting said detectable division;

wherein said motor is selectively deactivated a predetermined number of revolutions short of the overall desired number of revolutions to compensate for the coasting characteristics of the motor, said predetermined number of revolutions being a function of the ambient temperature sensed by said ambient temperature sensor;

wherein said means for controlling said heating means includes means for varying the heat generated by said heating means dependent upon the ambient temperature sensed by said ambient temperature sensor; and means associated with said controlling means for adjusting the breath alcohol content reading based on the time it takes the fuel cell to reach its maximum output.

* * * * *